US00PP18259P2

(12) United States Plant Patent
Van Zanten

(10) Patent No.: US PP18,259 P2
(45) Date of Patent: Nov. 27, 2007

(54) ***OSTEOSPERMUM* PLANT NAMED 'GG DEL PB06'**

(50) Latin Name: *Osteospermum ecklonis*
Varietal Denomination: GG DEL PB06

(75) Inventor: Leo Van Zanten, Oxnard, CA (US)

(73) Assignee: G + G Breeding Corporation, Oxnard, CA (US)

( * ) Notice: Subject to any disclaimer, the term of this patent is extended or adjusted under 35 U.S.C. 154(b) by 0 days.

(21) Appl. No.: 11/394,715

(22) Filed: Mar. 31, 2006

(51) Int. Cl.
*A01H 5/00* (2006.01)

(52) U.S. Cl. ..... Plt./360

(58) Field of Classification Search ..... Plt./360
See application file for complete search history.

*Primary Examiner*—Wendy C. Haas
*Assistant Examiner*—Georgia Helmer

(57) ABSTRACT

A new and distinct *Osteospermum* plant cultivar is disclosed, characterized by large daisy type inflorescences, freely flowering under outdoor growing conditions with continuous blooming from spring through autumn, light purple and white bi-color ray florets, and disc florets with dark blue at very center with light blue and light purple at the edges.

1 Drawing Sheet

Latin name of the genus and species: *Osteospermum ecklonis.*
Variety denomination: 'GG DEL PB06'.

BACKGROUND OF THE INVENTION

The new cultivar 'GG DEL PB06' is a product of open pollination in a heterogeneous population of *Osteospermum* mass selection. The new cultivar was discovered and selected by Leo Van Zanten in May 2004 in Carpinteria, Calif.

Asexual reproduction of the new cultivar 'GG DEL PB06' by cuttings from adventitious shoots was performed in Oxnard, Calif. and has shown that the unique features of this new cultivar are stable and reproduced true to type on successive generations.

SUMMARY OF THE INVENTION

The cultivar 'GG DEL PB06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG DEL PB06'. These characteristics in combination distinguish 'GG DEL PB06' as a new and distinct *Osteospermum* cultivar:

1. Large daisy type inflorescence;
2. Pale purple and white bi-colored ray florets;
3. Dark blue-violet disc florets.
4. A free branching habit.

There is not parent variety to compare to 'GG DEL PB06.'

In comparison to the commercially available variety 'Cape Daisy Volta' (U.S. Plant Pat. No. 10,338), 'GG DEL PB06' is smaller in both height and plant spread. Additionally, the individual leaves of 'GG DEL PB06' are much smaller than the comparable variety. Further, the new variety's ray florets are a darker purple and finally, the disc florets of 'GG DEL PB06' are violet-blue at the center with dark purple at the edges compared to the single color violet-blue disc florets of 'Cape Daisy Volta.'

BRIEF DESCRIPTION OF THE PHOTOGRAPH

The accompanying photograph drawing illustrates in full color a typical plant of 'GG DEL PB06' grown in a 6-inch pot, planted lake October and grown outdoors. The plant is 18 weeks old. The growing temperature ranged from 12° C. to 15° C. at night to 12° C. to 20° C. during the day. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG DEL PB06' plants grown in Oxnard, Ventura County, Calif., during the months of October through February. The growing temperature ranged from 12° C. to 15° C. at night to 12° C. to 20° C. during the day. Measurements and numerical values represent averages of typical flowering types.

Botanical classification: *Osteospermum ecklonis* cultivar 'GG DEL PB06.'

Commercial classification: Garden-type *Osteospermum.*

PROPAGATION

Time to rooting: 10 to 14 days at approximately 21° C.
Root description: Fine, fibrous.

PLANT

Growth habit: Mounding outwardly spreading herbaceous perennial.
Height: Approximately 24 cm.
Plant spread: Approximately 55 cm.

Growth rate: Vigorous.
Branching characteristics: Free Branching.
Length of lateral branches: Approximately 16 cm.
Number of leaves per lateral branch: Approximately 63.
Age of plant described: Approximately 127 days.

FOLIAGE

Leaf:
*Arrangement.*—Alternate single.
*Average length.*—Approximately 4.2 cm.
*Average width.*—Approximately 1.8 cm.
*Shape of blade.*—Obovate.
*Apex.*—Abruptly acuminate.
*Base.*—Attenuate.
*Attachment.*—Stalked.
*Margin.*—Entire with occasional tiny serrations.
*Texture of top surface.*—Lightly pubescent.
*Texture of bottom surface.*—Lightly pubescent.
*Leaf internode length.*—Approximately 2 cm.
*Color.*—Young foliage upper side: Near Green 137A. Young foliage under side: Near Green 137C. Mature foliage upper side: Near Yellow-Green 147A. Mature foliage under side: Near Green 137A.
*Venation.*—Type: Pinnate. Venation color upper side: Near Yellow-Green 144B. Venation color upper side: Near Yellow-Green 144B.

Petiole:
*Average length.*—Approximately 2.1 cm.
*Color.*—Near Yellow-Green 144B.
*Diameter.*—Approximately 0.3 cm.

BLOOM

Inflorescence:
*Flowering habit.*—Freely flowering under outdoor growing conditions with continuous blooming from spring through autumn and year round in a greenhouse environment.
*Inflorescence form.*—Daisy.
*Natural flowering season.*—Continuous throughout February to September in temperature regions.
*Number of inflorescences per lateral branch.*—Approximately 10.
*Inflorescence diameter.*—Approximately 7 cm.
*Inflorescence depth.*—Approximately 3 cm.
*Disc diameter.*—Approximately 1.5 cm.
*Inflorescence longevity on plant.*—Approximately 5 to 10 days; longevity of individual flowers are very dependent on temperature and light conditions.
*Persistence.*—Persistent.

Ray Florets:
*Appearance.*—Matte.
*Texture.*—Smooth.
*Average number of ray florets per inflorescence.*—22.
*Shape.*—Oblanceolate.
*Aspect.*—Slightly cupped, facing upward or outward.
*Margin.*—Entire.
*Apex.*—Obtuse.
*Length.*—Approximately 3.5 cm.
*Width.*—Approximately 1 cm.
*Color.*—Upper surface at first opening: Near Violet 83A at very base with near White 155A moving to Purple 75A at tip. Upper surface at maturity: Near Purple 79A at very base with shades of Purple 75D and White 155A moving to Purple 77C over half of the floret. Upper surface at fading: Near Purple 75B. Under surface at first opening: Near Violet 85D with shades of near Greyed-Yellow 162D. Under surface at maturity: Near Greyed-Purple 186D with longitudinal stripes of near Violet 86A. Under surface at fading: Near Greyed-Purple 186D with longitudinal stripes of near Violet 86A.

Disc Florets:
*Appearance.*—Matte.
*Texture.*—Smooth.
*Average number of florets per disc.*—Approximately 84.
*Shape.*—Tubular.
*Apex.*—Five-pointed.
*Average length.*—Approximately 0.5 cm.
*Average width.*—Approximately 0.1 cm.
*Color.*—At first opening: Near Violet-Blue 97A. At maturity: Near Violet-Blue 93C at very center with Purple 79A at edges. At fading: Mostly Violet-Blue 93A.

Peduncle:
*Length.*—Approximately 15 cm.
*Angle.*—Terminal peduncles, erect; secondary and tertiary peduncles, about 45° from vertical.
*Strength.*—Moderate.
*Color.*—Near Yellow-Green 147A with shades of Yellow-Green 147b.
*Habit.*—Upright.
*Diameter.*—Approximately 0.1 cm.
*Surface texture.*—Lightly pubescent.

Inflorescence Bud:
*Length.*—Approximately 1.9 cm.
*Diameter.*—Approximately 1 cm.
*Form.*—Elliptic.
*Color.*—Near Yellow-Green 150C.

Involucral Bracts (Phyllaries):
*Appearance.*—Matte.
*Texture.*—Lightly pubescent.
*Number.*—Approximately 15.
*Shape.*—Lanceolate.
*Margin.*—Entire.
*Apex.*—Narrowly acute.
*Length.*—Approximately 1.2 cm.
*Width.*—Approximately 0.2 cm.
*Color.*—Upper side: Near Green 137C. Under side: Near Green 138B.

REPRODUCTIVE ORGANS

*Androecium.*—Present on disc florets only. Number of stamens: 5. Anther shape: Linear. Anther length: Approximately 1.6 cm. Anther color: Near Purple 79A. Amount of pollen: Not abundant. Pollen color: Near Yellow-Orange 22A.
*Gynoecium.*—Present on ray and disc florets. Pistil Number: One. Pistil length: Approximately 6 mm. Stigma shape: Two parted. Stigma length: Approximately 1.3 mm. Stigma color: Near Purple 79A. Style length: Approximately 0.3 cm. Style color: Near Purple 76A.

OTHER CHARACTERISTICS

Disease resistance: Neither resistance nor susceptibility to diseases or pests has been observed in this variety.

Drought tolerance/cold tolerance: Plants are moderately drought tolerant. Plants need cold, less than 12.8° C. for flower induction.

Fruit/seed production: Commercially, this plant is not used or observed in a stage where seeds would be produced. Therefore, seed production has not been observed.

What is claimed is:

1. A new and distinct cultivar of *Osteospermum* plant named 'GG DEL PB06' as herein illustrated and described.

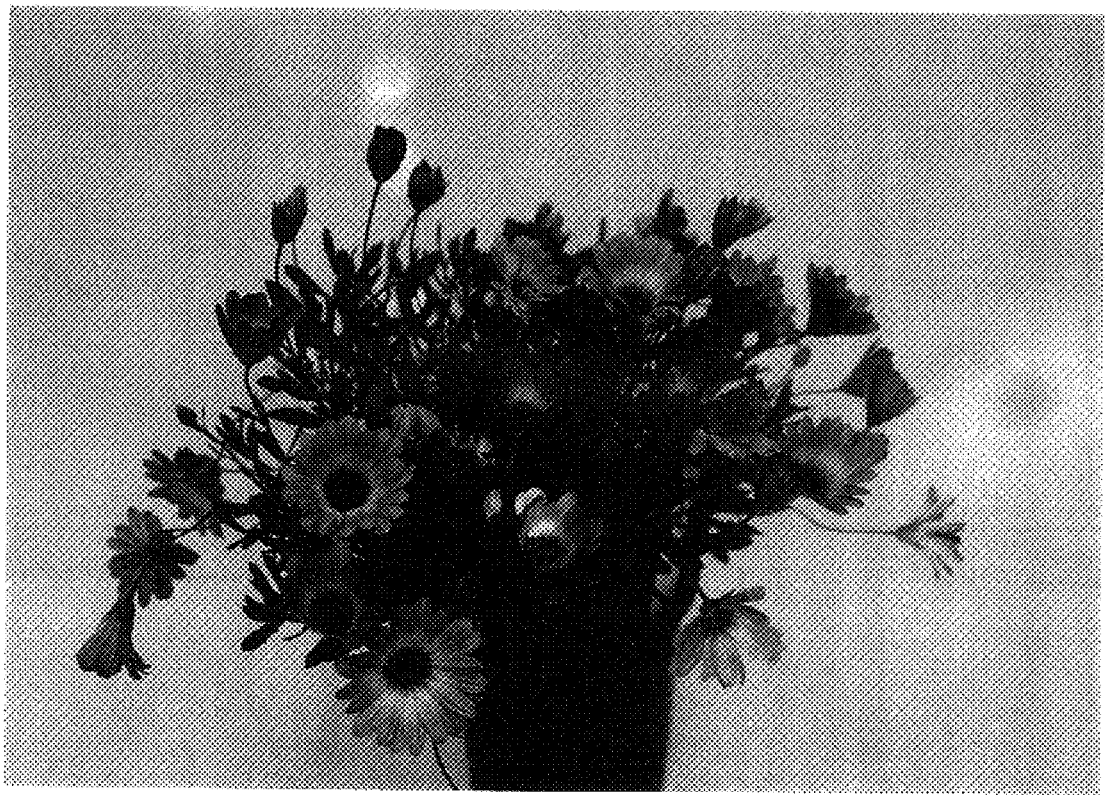

* * * * *